United States Patent [19]

Dau et al.

[11] Patent Number: 5,023,549
[45] Date of Patent: Jun. 11, 1991

[54] EDDY CURRENT PROBE WITH SENSOR SUPPORTING EXPANDABLE ELASTIC MEMBRANE FOR INSPECTING HOLLOW CYLINDRICAL STRUCTURES

[75] Inventors: Gary J. Dau, Palo Alto, Calif.; David C. Schiltz, Columbus; William R. Schneider, Athens, both of Ohio

[73] Assignee: Electric Power Research Institute, Inc., Palo Alto, Calif.

[21] Appl. No.: 319,962

[22] Filed: Mar. 7, 1989

[51] Int. Cl.[5] .................... G01N 27/82; G01N 27/90; G01R 33/12
[52] U.S. Cl. .................... 324/220; 324/262
[58] Field of Search .............. 324/219–221, 324/262; 376/245, 249

[56] References Cited

U.S. PATENT DOCUMENTS

| | | |
|---|---|---|
| 2,622,125 | 12/1952 | Bender .................... 324/220 |
| 2,622,126 | 12/1952 | Bender et al. .................... 324/220 |
| 3,916,302 | 10/1975 | Madewell .................... 324/220 |
| 4,063,157 | 12/1977 | Lorenzi et al. .................... 324/220 X |
| 4,105,972 | 8/1978 | Smith .................... 324/220 |
| 4,153,875 | 5/1979 | Pigeon et al. .................... 324/220 |
| 4,303,884 | 12/1981 | Malick .................... 324/220 |
| 4,668,912 | 5/1987 | Junker .................... 324/220 |
| 4,889,679 | 12/1989 | Snyder et al. .................... 324/220 X |

Primary Examiner—Gerard R. Strecker
Attorney, Agent, or Firm—James B. Hinson

[57] ABSTRACT

An eddy current sensor probe which includes first and second rigid end portions coupled together with a central portion comprising a flexible membrane. The flexible membrane includes indentations comprising sensor supporting regions. A differential pressure is applied across the membrane to position the sensors in a favorable location for collecting data related to the condition of the wall portion of hollow tubes.

7 Claims, 2 Drawing Sheets

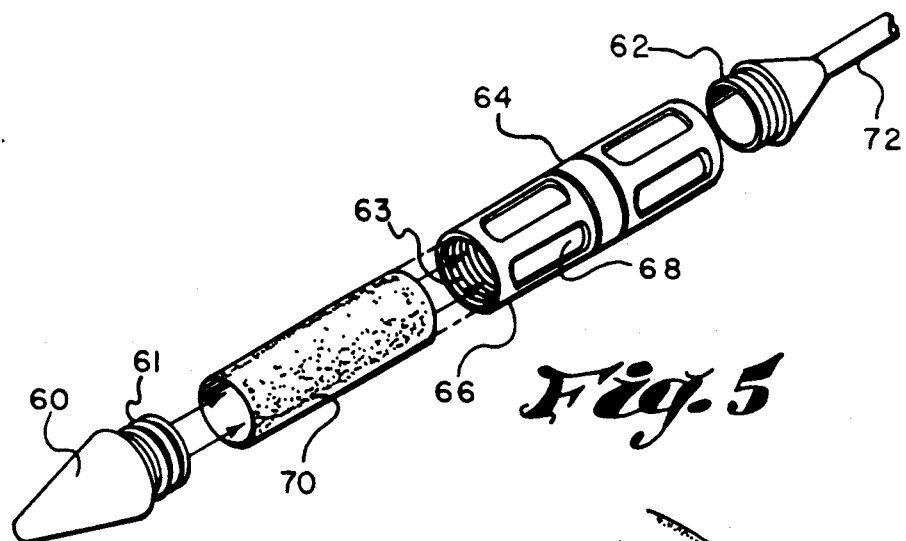
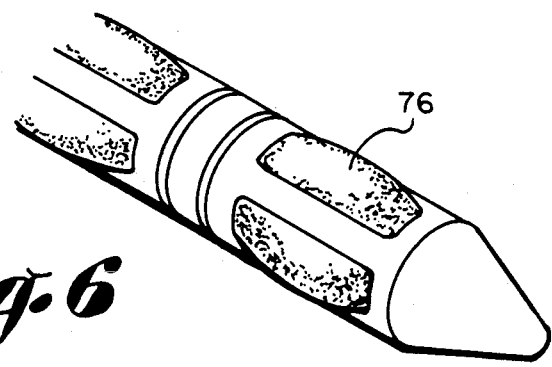
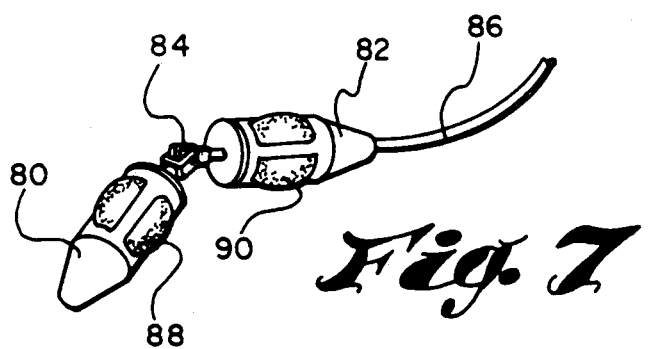
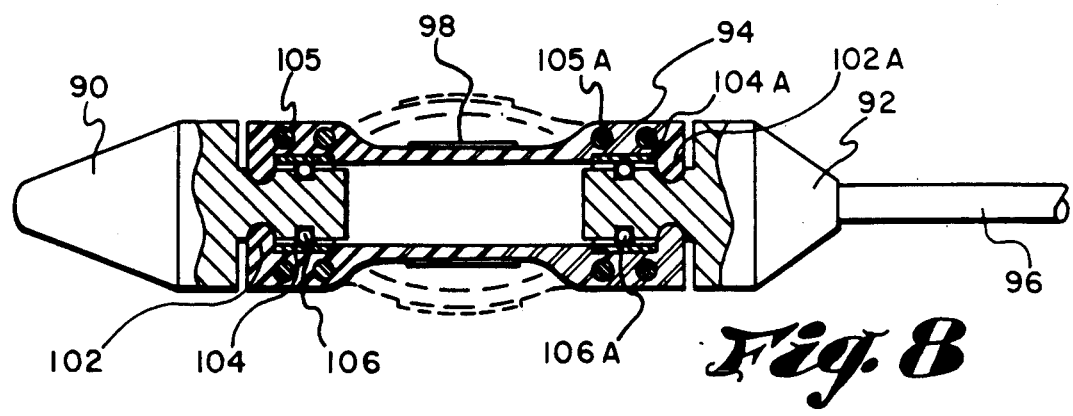

EDDY CURRENT PROBE WITH SENSOR SUPPORTING EXPANDABLE ELASTIC MEMBRANE FOR INSPECTING HOLLOW CYLINDRICAL STRUCTURES

BACKGROUND OF THE INVENTION

Field of the Invention

The invention relates to inspection devices and more particularly to eddy current probes for inspecting cylindrical structures.

SUMMARY OF THE INVENTION

Eddy current sensors are widely used to inspect components for defects. Typically, the eddy current sensors and supporting structures are referred to as an "eddy current probe". In all cases it is necessary to accurately position the eddy current sensors with respect to the components being inspected. Additionally, unintentional motion between the eddy current sensor and the component being inspected introduces errors, which may be of sufficient magnitude to render the results of the inspections unusable.

Inspection of hollow cylindrical structures, such as pipes and tubes, introduces additional problems. In some situations such structures may contain one or more bends which complicate the positioning of the eddy current probe. Deterioration of the interior surface, either by deposits or erosion, may further complicate accurate positioning of the eddy current probe with respect to the interior surface of the cylinderical structure being inspected. Additionally, typical surface deterioration can roughen the interior surface, causing abrasion of the outer surface of the eddy current probe as the probe is moved along the interior of the tubes. Each of these problems is ameliorated by the eddy current probe which is the subject matter of the invention.

Eddy current probes comprising various embodiments of the invention can easily be moved along the interior of cylindrical (hollow) structures to be inspected, including around bends. Pressure activated means is also provided to position the eddy current sensors in a fixed relationship to the interior of the structure being inspected during the time interval when test data is being collected. Surfaces of the eddy current probe supporting the eddy current sensors are protected from abrasion as the eddy current probe is moved along the interior of the structure increasing the useful life of the probe. These features significantly ameliorate the above problems with prior art eddy current probes.

DESCRIPTION OF THE PRIOR ART

A patent search was performed prior to preparing this patent application. During the search the following patents were noted as being of interest.

U.S. Pat. No. 4,303,884 discloses an eddy current probe for inspecting pipes in which the eddy current sensors are mounted on flexible strips and moved outwardly into contact with the interior of the pipe to be inspected.

U.S. Pat. No. 4,153,875, discloses an eddy current probe with the sensing coils supported between first and second guiding members which include resilient means for contacting the interior of the pipe to be inspected.

U.S. Pat. No. 4,105,972, disclosed a device for inspecting pipes which include flux-sensing devices held in contact with the interior of the pipe by springs.

U.S. Pat. No. 4,063,157, disclosed a magnetic testing device in which a magnetic recording tape is held against the interior of a pipe by an inflated elastic member.

U.S. Pat. No. 3,916,302, discloses a flexible multi-coil eddy current probe.

U.S. Pat. No. 2,662,126, discloses a probe which includes a flexible body member having radial recesses in which testing coils are positioned.

DESCRIPTION OF THE DRAWINGS

FIG. 5 is an exploded view of a second embodiment of the invention.

FIG. 6 is a drawing illustrating the expansion of selected surfaces of the eddy current probe to position the eddy current sensors in a fixed position relative to the interior of the tube being inspected.

FIG. 7 is a pictorial drawing of a multi-section eddy current probe.

FIG. 8 is a drawing illustrating another embodiment of the eddy current probe.

DETAILED DESCRIPTION

In many applications, it is desirable to inspect the interior of hollow cylindrical structures, such as tubes. Typical applications include the inspection of the interior of tubes used in various portions of nuclear power plants, such as steam generators. Such inspections are relatively complicated in that a typical steam generator will include a large number of individual tubes. Various tubes used in such applications may include curved portions. Additionally, environmental conditions inside the tube during use cause degradations which may include erosion, build-up of deposits or a combination of erosions and deposits. Such degradations further complicate inspections of such tubes from the interior. The present invention was developed as a result of a research program whose purpose was to improve apparatus and methods for inspecting tubes in the presence of these typical degradations.

Figure 1:
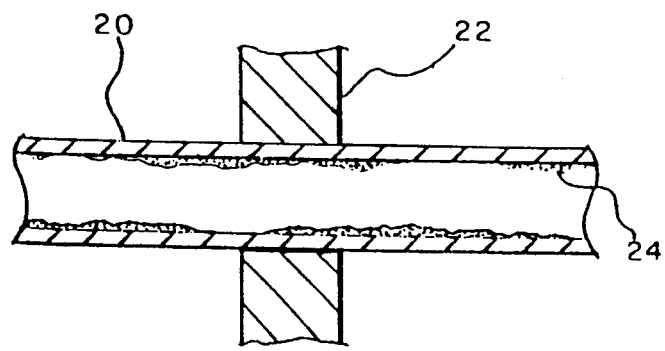
FIG. 1 is a cross-sectional drawing illustrating a typical tube having an irregular inner surface.
Figure 2:
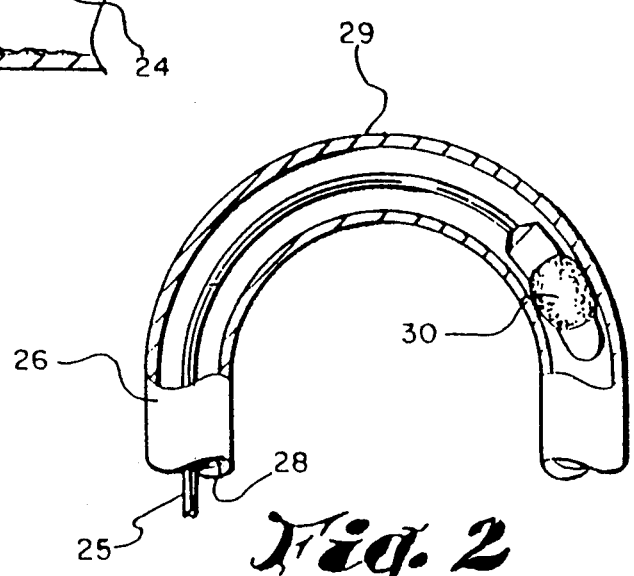
FIG. 2 is a drawing illustrating passage of the eddy current probe through a curved section of a tube.
Figure 3:
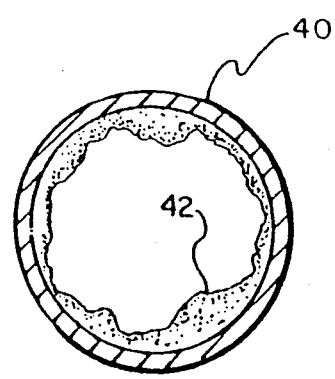
FIG. 3 is a horizontal cross-sectional drawing of a tube illustrating an irregular interior surface.

FIGS. 1 through 3 illustrate typical tubes including degradations. For example, FIG. illustrates a small cross-section of a typical tube 20 which passes through a sheet-like supporting member 22. A typical steam generator could include hundreds of tubes mounted in this manner. The interior surface 24 of the typical tube 20 is irregular with this irregularity due to erosions, build up of deposits or a combination of the two.

A typical tube section may also include curved portions, typically illustrated as semicircular tube 26 in FIG. 2. In inspecting all portions of the tube 26, the eddy current probe must be capable of being inserted into the first end 28 of the tube 26 and passed around the curved portion 29. For purposes of illustration, the eddy current probe is shown at position 30 after being passed around the curved portion 29 using an insertion and control cable 25.

FIG. 3 illustrates in cross section another typical tube segment 40. This section has an irregular inner surface 42 which may be caused either by erosion, build up deposits or both. All embodiments of the eddy probe are designed to be used to inspect tubes from the interior in the presence of curved and irregular interior surfaces, such as those typically illustrated in FIGS. 1 through 3.

As will be appreciated from the descriptions of FIG. 1 through 3, the eddy current probe must be capable of being passed through tubes whose interior surface is irregular in both the horizontal and radial directions. Additionally, as is well known in the art, it is necessary to position the eddy current sensors at a fixed position within the tube with respect to both the horizontal and radial directions in order to reduce noise and obtain measurement data which has a meaningful relationship to the condition of the tube being inspected. Stated another way, eddy current sensor sensitivity varies dramatically with spacing from the surface inspected, and mechanical movement of the eddy current sensor relative to the interior of the tube during inspection creates noise which may be sufficient to render the inspection data invalid.

The eddy current probes which are the subject of this invention are designed to accurately position eddy current sensors in order to obtain reliable data permitting the condition of the tube being inspected to be determined under the above described operating conditions.

Figure 4:
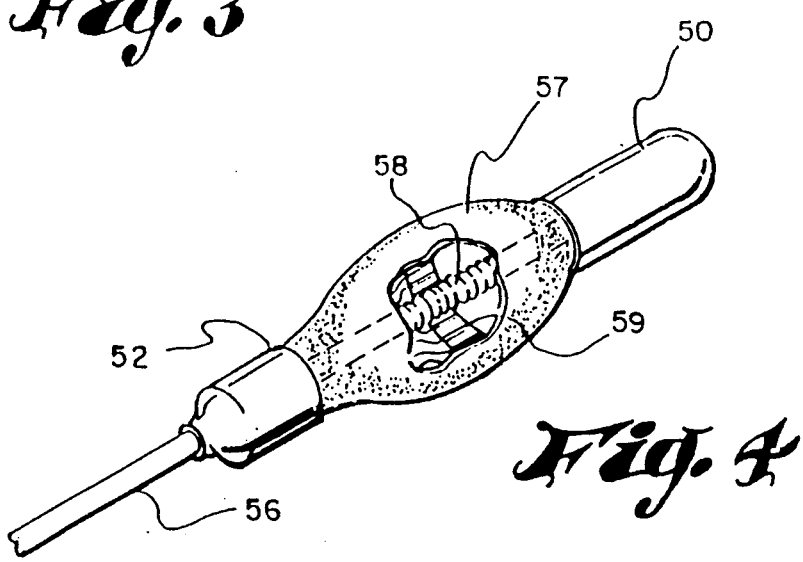
FIG. 4 is a pictorial drawing of one embodiment of the invention.

FIG. 4 is a pictorial drawing of a first embodiment of the invention. Fundamentally, the eddy current probe includes first and second rigid portions 50 and 52 which are coupled together a central flexible portion. The probe is inserted into and removed from the tube to be inspected by a flexible insertion and control cable 56.

More specifically, the central portion includes a central relatively flexible member 58 surrounded by an elastic membrane portion 57. A plurality of eddy current sensing elements are, supported by the elastic membrane 57, with a typical eddy current sensor functionally illustrated at reference numeral 59. An insertion and control cable 56 is used to insert, remove and control the eddy current probe. If the elastic membrane 57 is rubber, plastic or other similar material, the eddy current sensor 59 may be embedded in the elastic membrane 57 or support by its surface. Cable and insertion cable 56 also includes all of the supporting apparatus necessary to control and operate the eddy current sensors 59 and the eddy current probe.

For example, the insertion and control cable 56 includes suitable tubing or conduits for controlling the differential pressure across the elastic membrane 57 to selectively change its outer diameter. Suitable wiring to operate the eddy current sensors is also included.

To facilitate insertion or movement of the eddy current probe through the interior of the tube 26, the differential pressure across the elastic membrane 57 is decreased causing its diameter to decrease to a diameter less than the minimum inside diameter of the tube 26. In this configuration, the eddy current probe is easily moved through the tube 26 to the desired position using the insertion and control cable 56. When the eddy current probe has been moved into the desired position, the differential pressure across the elastic membrane 57 is increased, causing the elastic membrane 57 to expand moving eddy current sensors 59 out radially until the outer surface of the elastic membrane 57 contacts the interior surface of the tube 26. The differential pressure across the elastic membrane 57 is maintained to hold the elastic membrane 57 in this position while the eddy current sensors 59 are operated in a normal fashion to collect data indicative of characteristics of the tube 26 in regions adjacent to the eddy current sensors. Postioning the outer surface of the elastic membrane 57 in contact with the inner surface of the tube to be inspected, positions the eddy current sensors 59 in a stable and fixed relationship to the surface being inspected. As a result, the sensitivity of the eddy current sensor is enhanced and noise is reduced. Suitable tubing incorporated into the insertion and control cable 56 provides means for controlling the differential pressure across the elastic membrane 57.

FIG. 5 is a second embodiment of the invention. In this embodiment, a first rigid portion 60 is spaced from a second rigid portion 62 by an intervening relatively rigid portion 64. The central rigid portion 64 includes an outer hollow cylindrical portion 66 having a plurality of radially spaced elongated openings, with a typical elongated opening illustrated at reference numeral 68. Hollow cylindrical portion 66 is attached to end portions 60 and 62 using any convenient means, such as threaded portions 61 and 63. An elastic membrane 70 is positioned on the interior of the central portion 64 with the eddy current sensors supported by the elastic membrane 70. As with other embodiments, the eddy current sensors may be embedded in or supported by the elastic membrane 70. The entire probe is positioned into and moved through the tube to be inspected by an insertion and control cable member 72. The exterior surface of the elastic membrane 70 is designed to conform to the inner surface of the central portion 66 when the differential pressure across the elastic membrane 70 is equalized. When the deferential pressure of the elastic membrane 70 is increased, the elastic membrane expands and forms a substantially gas-tight seal with the cylinderical portion 66.

In operation, the insertion and control cable 72 includes all the wiring necessary to operate and control the eddy current sensors. Additionally, it includes suitable tubing permitting the differential pressure across the elastic membrane 70 to be controlled. More specifically, to move the eddy current probe through the tubes to be inspected, the differential pressure across the elastic membrane 70 is equalized, permitting the surfaces of the elastic membrane 70 to retract to approximately conform to the interior surface of the central portion 64. In this position, the eddy current probe can be moved through the tube conveniently with the elastic membrane 70 protected from abrasion by the rigid portion 64 which has a larger diameter than the elastic membrane 70. With the eddy current probe positioned at a point where inspections are to be made, the differential pressure across the elastic membrane 70 is increased causing the elastic membrane 70 to bulge out through the elongated openings 68 to position elastic membrane 70 in contact with the interior surfaces of the tube. Contact between the elastic membrane 70 and the interior surface of the tube being inspected holds the eddy current sensors in a fixed position with respect to the tube being inspected.

The expansion of the elastic membrane 70 to position the sensors is illustrated in fragmentary drawing FIG. 6. Bulging portions of the elastic membrane 70 are typically illustrated at reference numeral 76. Measurements are made With the elastic membrane 70 in contact with the interior of the tube to be inspected by operating the eddy current sensors in a conventional mode.

FIG. 7 illustrates a multi-section embodiment of the eddy current probe. In this embodiment, the eddy current probe consist of two relatively short rigid sections 80 and 82, coupled together by a flexible coupling 84. Flexible coupling 84 provides flexibility permitting the probe to be more easily moved through tubes to be inspected. The entire eddy current probe is positioned in and removed from teh tube to be inspected by a relatively flexible insertion and control cable 86. Each of the sections, 80 and 82, includes a rigid cylindrical member having elongated outer openings through which an elastic membrane, similar to the elastic membrane 70 illustrated in FIG. 5, can be expanded through the use of differential pressure to position the eddy current sensors supported by the elastic membrane in contact with the interior of the tube to be inspected. The expansion of the elastic membrane through typical openings is illustrated at reference numerals 88 and 90. The eddy current sensors, which may be positioned in all sections of the probe are operated to collect inspection data with the elastic membrane in this position. This embodiment of the invention permits a plurality of spaced eddy current sensors to be operated simultaneously to obtain additional data without significantly complicating the test process.

FIG. 8 illustrates another embodiment of the invention. This embodiment also includes first and second rigid members 90 and 92, coupled together by a central elastic membrane 94. The eddy current probe is positioned into and removed from the tube to be inspected by an insertion and control cable 96. Additionally, the insertion and control cable 96 includes electrical conductors permitting the sensors to be operated and tubes permitting the differential pressure across the elastic membrane 94 to be changed to selectively expand the central portion 94 to position the sensors 98 in a fixed position to the surfaces to be inspected.

The elastic membrane 94 is preferably made of relatively elastic material, such as rubber. Spaced radially around the exterior of the elastic member 94 are a series of indentations which are elongated longitudinally to create elongated indentations in the outer surfaces of the elastic membrane 94. Eddy current sensors are positioned in these indented elongations with a typical sensor being illustrated at reference numeral 98. Increasing the differential pressure across the elastic membrane 94 causes the indented portion to selectively expand and contact the interior surface of the tube being inspected. Selective expansion of the indentations may be achieved by making these regions thinner, as illustrated, or by other suitable structural means. Alternatively, the eddy current sensors may be embedded in the elastic membrane 94.

The elastic membrane 94 also includes substantially identical first and second end portions permitting the elastic membrane 94 to be attached to the first and second rigid portions 90 and 92. Due to this identity, only one of these end portions will be described in detail. Features of the second end are identified with the same reference numerals used to identify the corresponding feature of the first end followed by a letter "A".

The first end of the elastic membrane 94 includes an inwardly extending lip portion 102 which extends into a groove in the first rigid member 90. Disposed on the interior of the elastic membrane 94 and adjacent to the lip portion 102 is a relatively rigid ring portion 104. An "0" ring 106 is disposed in a groove in the rigid portion 90 and mates with the interior of the ring 104 to provide a pressure seal between the rigid member 90 and the elastic membrane 94. Additionally, if desired, stiffeners such as fabric strands 105 can be embedded in and extend radially around the elastic membrane 94 to provide additional rigidity. Additional rigidity may be required in the end portions of the elastic membrane 94 to assure that the inwardly extending lip portion maintains the eddy current probe assembled, as illustrated in FIG. 8. The seal assures that the required differential pressure can be maintained across the elastic membrane 94 without excessive leakage. Inwardly extending lip portion 102 has sufficient rigidity to maintain the elastic membrane 94 and the end portion 90 and 92 assembled, as illustrated in FIG. 8.

We claim:

1. An eddy current sensors probe adapted to be positioned within a hollow member having an unknown interior contour to perform measurements related to the characteristics of said hollow member, comprising in combination:
    a) at least a rigid portion having a first cylindrical end;
    b) at least a second rigid portion having a second cylindrical end;
    c) a central portion including a flexible membrane coaxially positioned with respect to said first and second rigid portions and having first and second end portions, said end portions having a first outer diameter, said flexible membrane also having at least a plurality of elongated indentations in its outer surface, said indentations being disposed between said first and second end portions, said indentations comprising expandable sensor supporting regions with a plurality of radially disposed eddy current sensors embedded therein, the outer surface of said sensor supporting regions having a second outer diameter, said second diameter being less than said first outer diameter, said first and second end portions of said membrane being respectively attached to said first and second ends of said first and second rigid portions, at least said sensor supporting regions selectively expanding in response to a differential pressure across at least said sensor supporting regions to radially position said eddy current sensors in a first position with respect to the interior surface of said hollow member permitting said sensors to be utilized to collect data related to the structural characteristics of said hollow member and in a second position which places said sensor supporting regions at a radial distance less than the outer diameter of said first and second end portions of said membrane thereby permitting said eddy current probe to be moved through said hollow member with contact between the inner wall of said hollow member and said sensor probe being substantially limited to portions having a radial diameter greater than the radial diameter of said sensor supporting regions.

2. An eddy current probe in accordance with claim 1 wherein the end portions of said membrane are rigid end portions mating with said first and second rigid portions to form a seal therewith, said seal supporting said differential pressure.

3. An eddy current probe in accordance with claim 2 wherein said rigid end portions of said membrane include radially disposed flexible non expandable members embedded therein.

4. An eddy current probe in accordance with claim 3 wherein said rigid end portions of said membrane also include cylindrical members affixed to the inner surface of said end portions, said cylindrical members cooperating with a sealing ring to produce said seal between said membrane and said first and second rigid portions.

5. Eddy current probe apparatus adapted to be positioned within a hollow structure having an unknown interior contour to perform test and produce data having a predetermined relationship to the characteristics of said structure, comprising in combination,
 a) at least a first rigid portion having a diameter less than the expected minimum internal diameter of said hollow structure;
 b) at least a second rigid portion having a diameter less than the expected minimum internal diameter of said hollow structure;
 c) a central portion comprising a hollow cylindrical outer portion having an outer diameter less than the inner diameter of the structure to be inspected, coaxially positioned with a flexible membrane portion of smaller diameter than said hollow cylindrically portion, said hollow cylindrically outer portion also including elongated openings therein, first and second ends of said central portion being respectively attached to an end of said first and second portions, said membrane portion being adapted to support sensors such that a differential pressure across said membrane causes the diameter of said membrane to selectively change to expand said membrane outwardly through said elongated openings to position said eddy current sensors in a fixed position with respect to the interior surface of a structure to be inspected.

6. Eddy current probe apparatus in accordance with claim 5 wherein said membrane expands outwardly to form a seal with said cylindrically portion as the differential pressure across said membrane increases.

7. Eddy current probe apparatus in accordance with claim 6 wherein said central portion includes a plurality of sections joined by a flexible coupling.

* * * * *